United States Patent [19]

Bennett

[11] 4,006,226
[45] Feb. 1, 1977

[54] ANTICONVULSANT DIPHENYLSILANES
[75] Inventor: Donald R. Bennett, Midland, Mich.
[73] Assignee: Dow Corning Corporation, Midland, Mich.
[22] Filed: Mar. 15, 1976
[21] Appl. No.: 666,822

Related U.S. Application Data
[63] Continuation-in-part of Ser. No. 587,029, June 16, 1975, abandoned.

[52] U.S. Cl. .............................................. 424/184
[51] Int. Cl.$^2$ ...................................... A61K 31/695
[58] Field of Search .................................... 424/184

Primary Examiner—Stanley J. Friedman
Attorney, Agent, or Firm—Norman E. Lewis

[57] ABSTRACT

Suppression of convulsions in warm-blooded animals is accomplished by administration of diphenylsilanes of the formula $\phi_2SiX_2$ in which X is a hydroxyl group or one of several readily hydrolyzable radicals, such as the methoxy group.

19 Claims, No Drawings

ANTICONVULSANT DIPHENYLSILANES

This application is a continuation-in-part of application Ser. No. 587,029 filed June 16, 1975, now abandoned.

The present invention relates to a method of suppressing convulsions in warm-blooded animals. In one aspect, the invention relates to a method of combating epileptic seizures.

This invention is based on the unexpected finding that certain diphenylsilanes, when administered to warm-blooded animals, exhibit anticonvulsant activity. "Anticonvulsant activity", of course, is the ability of a compound to terminate or arrest convulsive episodes — or, in a further sense, to prevent or suppress the incidence of convulsive seizures in patients, such as those suffering from epilepsy.

Thus, the present invention provides a method of suppressing convulsions in a warm-blooded animal which comprises administering to such an animal a silane of the formula $\phi_2SiX_2$ in which X is a hydroxyl group or a radical which is capable of hydrolyzing in vivo to form the hydroxyl group; said silane being administered in amount sufficient to suppress convulsions in the animal.

The diphenylsilanes useful in the practice of the above-described method are $\phi_2Si(OH)_2$ and certain precursors to the diol. These precursors contain one or two silicon-bonded radicals which hydrolyze in the gastrointestinal tract or bloodstream to give rise to the active diphenylsilanediol.

Hydrolyzable groups attached to organosilicon compounds are numerous and well-known in the art. Generally these groups are organic moieties such as hydrocarbonoxy radicals but other groups such as $-NH_2$ and $-ONa$ do not fit the classic definition of "organic". Those radicals which hydrolyze (or react with water) in vivo to form the $\equiv SiOH$, include the hydrogen atom, alkoxy radicals of the formula $-OR$ in which R is an alkyl of from 1 to 3 inclusive carbon atoms and acyloxy radicals of the formula $$-OCR', \\ \parallel \\ O$$

in which R' is an alkyl radical or an aryl-containing monovalent hydrocarbon radical, including aryl, alkylaryl and arylalkyl groups. Further examples of readily hydrolyzable groups are amine radicals of the formula $-NR''_2$ in which R'' is a hydrogen atom or an alkyl or aryl-containing hydrocarbon radical as described above; aminoxy radicals of the formula $-ONR''_2$; ketoxime radicals of the formula $-ON=CR'_2$, amido radicals of the formula $$-N(R'')-C-R', \\ \parallel \\ O$$

imine radicals of the formula $$-NH-C-R' \text{ and} \\ \parallel \\ NH$$

and thioamide radicals such as $$-NH-C-R' \\ \parallel \\ S$$

In addition to $\equiv Si-O-C$ and $\equiv Si-N-$ bonding, the $\equiv Si-S-$ bond is hydrolyzable, with sulfur-containing hydrolyzable groups being represented by radicals of the formulae $$-SR', \ -S-CR' \text{ and } -S-CR'. \\ \phantom{-SR',\ }\parallel \phantom{ \text{ and } -S-}\parallel \\ \phantom{-SR',\ }O \phantom{ \text{ and } -S-}S$$

The $\equiv SiO-M$ bond, wherein M is an alkali metal or an ammonium radical, is also hydrolyzable. Exemplary of hydrolyzable $-OM$ radicals are $-ONa$, $-OK$, and $OLi$ or, $-ONR_4''$ such as $-ONH_4$.

It is apparent from this listing that the $\equiv SiC-$ bond does not react with water and radicals such as $-CH_3$ and $-C_6H_5$ are not considered "hydrolyzable groups". It is also to be noted that certain groups which hydrolyze very slowly or only under extreme conditions do not hydrolyze in vivo at a rate sufficient to provide diol or exhibit anticonvulsant activity. The butoxy radical is one such group. To provide miscibility and solubility in liquid pharmaceutical carriers it is preferred that the R' and R'' hydrocarbon radicals are alkyl radicals of 1 to 20 carbon atoms or aryl-containing monovalent hydrocarbon radicals of from 6 to 9 carbon atoms. As will be apparent from further examples, the X group need not be the same. Compounds containing $=Si(OH)H$ and $=Si(OC_2H_5)H$ can be utilized in the practice of the invention.

The above-listing of readily hydrolyzable radicals is not intended to be all inclusive. Other such hydrolyzable radicals, such as cyclized acyloxy, mercapto, or amines; for example

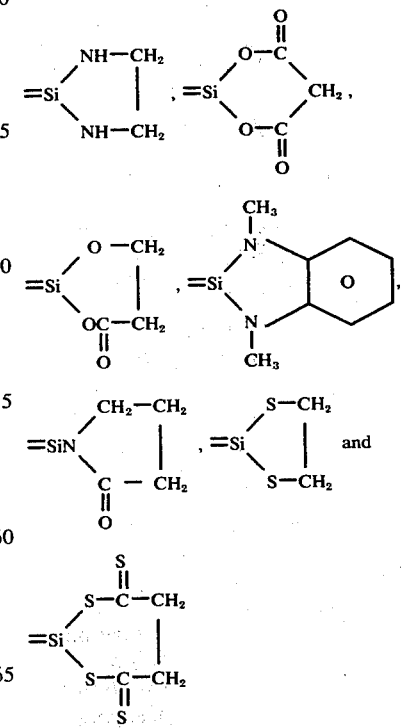

are also available.

Exemplary of the preferred and most readily available silanes are

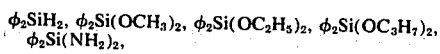

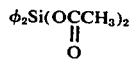

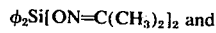

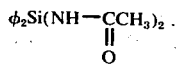

In view of the well-developed state of the art relating to organosilanes, further description would be repetitious.

The diphenylsilanes are readily synthesized by well-known techniques involving hydrolysis of the corresponding dichlorosilane or by reacting the dichlorosilane with compounds giving rise to the desired hydrolyzable group. For example, diphenyldichlorosilane is reacted with the corresponding alcohol to obtain the described dialkoxysilanes. Diphenylsilanediol is a crystalline solid while the hydrolyzable silanes are low viscosity liquids.

The defined silanes can be administered in any pharmaceutically acceptable manner by either the oral or parenteral route. The dose form of the silane can include pharmaceutically acceptable carriers and other conventional adjuvants. The dosage may be administered orally in such forms as tablets, capsules, suspensions and the like or parenterally in the form of an injectable suspension or solution. Suitable pharmaceutical carriers include liquids, such as water or oils of animal, vegetable or synthetic origin, for example peanut oil, mineral oil, sesame oil and the like; aqueous dextrose and related sugar solutions and glycols, such as propylene glycol. Inert solid carriers, such as calcium carbonate, calcium phosphate, starch, lactose and the like can also be utilized. Other pharmaceutical carriers are listed in "Remington's Pharmaceutical Sciences" by E. W. Martin, a well-known reference in this field.

The silanes are administered in amounts effective to suppress convulsions in warm-blooded animals, such as mice, rats, gerbils, dogs, monkeys and humans. The optimum anticonvulsant amount will vary with the particular silane (or mixtures thereof) utilized, with the size and species of animal treated, and with the severity (both as to duration and frequency) of the convulsive episodes suffered by the animal. Dosages of about 5 to 100 mg./kg. of body weight are generally sufficient to prevent or reduce the incidence of convulsive seizures. Suggested unit dosages for larger animals are 100 to 500 mg. of silane per tablet or capsule or 25 to 150 mg. of silane/cc. of solution or dispersion. In any event, the effective amount is well below the toxic amount ($LD_{50}$) of the silane compound. The effective amount is also well below those amounts which give undesirable neurological side effects, such as complete sedation.

Of course, it is within the scope of the invention to administer a mixture of silanes as a method of suppressing convulsions. The weight ratio of different silanes in the mixture may vary depending upon the above noted factors and the effective amount will be the same as previously described. The combination of $\phi_2Si(OH)_2$ with $\phi_2SiH_2$ or $\phi_2Si(OH)(OCH_3)$ with $\phi_2SiH(OH)$ are examples of such mixtures.

The following examples are illustrative of the anticonvulsant activity of the diphenylsilanes utilized in the practice of the present invention.

EXAMPLE 1

The electroshock test procedure was used to determine anticonvulsant activity of diphenylsilanediol. Adult female mice (Swiss Webster strain) were utilized as test animals. With administration of 60 Hz A.C. interrupted shocks of 0.2 second duration of 50 milliamp, all untreated mice demonstrated tonic extension of the hind limbs. Seizure protection was scored as inhibition of tonic extension. Groups of mice (six/group) were dosed interperitonially with varying amounts of diphenylsilanediol in a 0.5% methylcellulose solution in distilled water. The dosages ranged from 10 to 100 mg./kg. and the electroshock was applied 30 minutes after dosing. The effective dose to prevent convulsions in half the animals ($ED_{50}$) was determined to be 20 mg./kg. and the 95% CI (confidence interval) was 15.1 to 24.9 mg./kg.

Further testing of groups of mice (six/group) in triplicate showed the peak time of the anticonvulsant effect for a dose of 25 mg./kg. ($ED_{99}$) to be 30 minutes after dosing, the half time of the effect to be about four hours, with some measurable anticonvulsant activity being noted up to 10 hours. The toxicity ($LD_{50}$) of this silane solution (as freshly prepared) in mice, administered i.p., was determined to be 2500 mg./kg.

Mice were also dosed with a similar solution of diphenylsilanediol but by intravenous administration. The $ED_{50}$ was determined to be 10 mg./kg. with a 5 minute peak time by a modified maximal electroshock technique in which stimulus was delivered at 100 Hz for 0.1 second at 150 volts.

Oral dosing of mice via gastric intubation with the diphenylsilanediol suspended in sesame oil solution was also performed. Maximal electroshock (modified as described above) was again used to determine the amount necessary to provide an effective dose ($ED_{50}$) at various time intervals after dosing. Results as determined by dosing of a total of 180 mice are as follows:

| Time After Dosing | 2 hrs. | 4 hrs. | 6 hrs. |
|---|---|---|---|
| $ED_{50}$ (mg./kg.) | 25 | 37 | 60 |

Thus it is apparent that the silane can be effectively administered by a number of routes and in different carriers. Both the effective dose and peak time of anticonvulsant activity vary with the route of administration and specific vehicle.

EXAMPLE 2

Diphenylsilanediol was also tested to determine its effectiveness against chemically-induced seizures. Pentylenetetrazol and strychnine were the convulsant compounds used. Pentylenetetrazol testing was performed in accordance with Swinyard's method as described in J. Am. Pharm. Assoc. 38:201, 1949, while styrchnine tests were made by the method of Everett and Richards as described in J. Pharm. Exp. Ther. 81:402, 1944.

The silane (in 0.5% aqueous methylcellulose) was administered i.p. to groups of 6 mice (female Swiss Webster) at doses of 10, 30, 100 and 300 mg./kg. The silane solution was administered 30 minutes before injection with one of the convulsant drugs. The end point for scoring effectiveness was the absence of clonic seizures during the 30 minute period subsequent to administration of the convulsant — this same criterion was utilized in conducting the strychnine tests. In both tests, effective amounts ($ED_{50}$) of the silane were equivalent with the pentylenetetrazol-induced convulsion requiring 58 mg./kg. and the styrchnine tests showing 60 mg./kg. as the $ED_{50}$.

carrier. Sesame oil was used to ensure that hydrolysis did not occur prior to dosing. The effective amount ($ED_{50}$) for the compounds at three different time intervals after dosing was determined as previously described.

The $LD_{50}$ of certain silanes was determined by administering a single dose of the silane in sesame oil to groups of the male mice. The animals were observed for 14 days with no further dosing, the number dead at each dose level after this period being used to determine the $LD_{50}$.

Results ($ED_{50}$ and $LD_{50}$) for the various silanes are tabulated below:

Table

| Compound | Time (Hrs.) After Dosing | Maximal Electroshock $ED_{50}$(mg./kg. - (95% C.I.) | $LD_{50}$ (mg./kg.) |
|---|---|---|---|
| $\phi_2Si(OCH_3)_2$ | 2 | 39 (27–52) | |
| | 4 | 26 ( 1–43) | 1060 |
| | 6 | 52 (10–88) | |
| $\phi_2Si(OC_2H_5)_2$ | 2 | 37 (18–55) | |
| | 4 | 50 (25–71) | 1720 |
| | 6 | 22 ( 3–53) | |
| $\phi_2Si(On-C_3H_7)_2$ | 2 | no protection | |
| | 4 | 89 (22–407) | 1000 |
| | 6 | 32 ( 9–69) | |
| $\phi_2Si(Oi-C_3H_7)_2$ | 2 | no protection | |
| | 4 | 99 (43–308) | 990 |
| | 6 | 66 (39–122) | |
| $\phi_2Si(NH_2)_2$ | 2 | 56 (27–117) | |
| | 4 | 68 (32–142) | — |
| | 6 | 100 (47–211) | |
| $\phi_2Si(OCCH_3)_2$ $\overset{\|}{O}$ | 2 | 43 (15–75) | |
| | 4 | 11 ( — ) | — |
| | 6 | 50 (23–105) | |
| $\phi_2SiH_2$ | 2 | 28 (10–62) | |
| | 4 | 25 (8–53) | 924 |
| | 6 | 28 (8–60) | |
| $\phi_2Si(NCH_3)_2$ $\|$ H | 2 | 68 (32–150) | |
| | 4 | 70 (33–155) | — |
| | 6 | 153 (72–367) | |
| $\phi_2Si[N(CH_3)_2]_2$ | 2 | 50 (23–105) | |
| | 4 | 50 (23–105) | — |
| | 6 | 56 (27–117) | |
| $\phi_2Si[OCH_2CH_2N(C_2H_5)_2]_2$ | 2 | 52 (21–128) | |
| | 4 | 84 (60–202) | — |
| | 6 | 168 (34–412) | |
| $\phi_2Si(SC_4H_9)_2$ | 2 | 290 (130–690) | |
| | 4 | 65 (22–193) | — |
| | 6 | 65 (22–193) | |
| $\phi_2Si\begin{smallmatrix}H\\ \\OC_2H_5\end{smallmatrix}$ | 2 | 22 (10–46) | |
| | 4 | 21 (1–48) | — |
| | 6 | 46 (14–141) | |
| $\phi_2Si(ONa)_2$ | 2 | 37 (23–52) | |
| | 4 | 61 (39–94) | — |
| | 6 | 90 (58–146) | |
| Mixture 50% $\phi_2Si(OH)_2$ 50% $\phi_2SiH_2$ | 2 | 23 (15–34) | |
| | 4 | 29 (17–45) | — |
| | 6 | 39 (26–54) | |
| *HOSiOSiOH with $\phi$ $\phi$ substituents | 2 | 1000 | |
| | 4 | 1000 | — |
| | 6 | 1000 | |
| *$\phi_2Si(On-C_4H_9)_2$ | 2 | no protection | |
| | 4 | 1000 | 5300 |
| | 6 | 1000 | |

*for purposes of comparison

This data, when taken in conjunction with the electroshock data of Example 1, demonstrate that the silane exhibits anticonvulsant activity against a variety of seizure mechanisms.

EXAMPLE 3

The modified (100 Hz, 0.1 sec., 150 volt) maximal electroshock test was used to determine the anticonvulsant activity of several hydrolyzable silanes. Male Carworth mice were used as the test animal. All of the compounds were administered orally in a sesame oil While the readily hydrolyzable silanes are effective anticonvulsants, it is apparent that diphenylsilanes containing radicals which hydrolyze in vivo at a very slow rate, such as the diphenyl-di-n-butoxysilane have no observed activity. It is also apparent that the condensation product of diphenylsilanediol,

has no anticonvulsant activity.

EXAMPLE 4

A young adult dog (German Shepard) was diagnosed as having idiopathic epilepsy after having grand mal seizures of the clonic type. Attempts to control the seizures with a combination of pheobarbital, primidone and diphenylhydantoin were not successful since the effective anticonvulsant amount also produced sedation of the 25 kilogram animal.

Replacement of the above regimen with administration of 500 mg. of diphenylsilanediol (in 0.5% aqueous methylcellulose) given intramuscularly twice per day was effective in controlling seizures in the dog. After five days of dosing, the same amount was administered orally in 250 mg. capsules for a period of 10 days. The dog did not experience seizures during this 15 day period. When dosing was discontinued, the first seizure occured 39 hours after the last dose and then seizures were experienced at about four-hour intervals. Reinstitution of the diphenylsilanediol regimen, at one-half the previous dosage orally was effective in eliminating seizures. Upon cessation of the 10 mg./kg. oral dose twice daily after 10 days, the dog experienced its first seizure 30 hours postdose with seizures continuing every three hours.

These data suggest that the silane is longer-lasting in the dog than in rodents and, further, that the silane is also potent in controlling seizures due to idiopathic mechanism.

Reasonable modification and variation are within the scope of the invention which is directed to a method of suppressing convulsions in an animal by providing diphenylsilanediol in the animal by either the diol or a hydrolyzable precursor of the diol.

That which is claimed is:

1. A method of suppressing convulsions in a warm-blooded animal comprising administering to said animal a diphenylsilane of the formula $\phi_2SiX_2$ in which X is a hydroxyl group or a radical which hydrolyzes in vivo to form the hydroxyl group, said silane being administered in amount effective to suppress convulsions in the animal.

2. A method in accordance with claim 1 wherein the silane is diphenylsilanediol.

3. A method in accordance with claim 1 wherein a mixture of diphenylsilanes is utilized.

4. A method in accordance with claim 3 wherein the mixture is $\phi_2Si(OH)_2$ and $\phi_2SiH_2$.

5. A method in accordance with claim 1 wherein the silane is a hydrolyzable silane in which X is a radical which hydrolyzes in vivo to form the hydroxyl group.

6. A method in accordance with claim 5 wherein the silane is of the formula $\phi_2SiH_2$.

7. A method in accordance with claim 5 wherein the hydrolyzable silane is of the formula $\phi_2Si(OR)_2$ in which R is an alkyl radical of from 1 to 3 inclusive carbon atoms.

8. A method in accordance with claim 5 wherein the hydrolyzable silane is of the formula $\phi_2Si(NH_2)_2$.

9. A method in accordance with claim 5 wherein the hydrolyzable silane is of the formula

10. A method in accordance with claim 5 wherein the hydrolyzable silane is of the formula

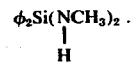

11. A method in accordance with claim 5 wherein the hydrolyzable silane is of the formula $\phi_2Si[N(CH_3)_2]_2$.

12. A method in accordance with claim 5 wherein the hydrolyzable silane is of the formula $\phi_2Si[OCH_2CH_2N(C_2H_5)_2]_2$.

13. A method in accordance with claim 5 wherein the hydrolyzable silane is of the formula $\phi_2Si(SC_4H_9)_2$.

14. A method in accordance with claim 5 wherein the hydrolyzable silane is of the formula

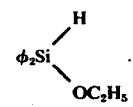

15. A method in accordance with claim 5 wherein the hydrolyzable silane is of the formula $\phi_2Si(ONa)_2$.

16. A method in accordance with claim 1 wherein the silane is administered in combination with a pharmaceutically acceptable carrier.

17. A method in accordance with claim 1 wherein the silane is administered orally.

18. A method in accordance with claim 1 wherein the silane is administered parenterally.

19. A method in accordance with claim 1 wherein diphenylsilanediol is administered in an amount in the range of from about 5 to 100 mg./kg. of animal body weight.

* * * * *